US00PP34723P2

(12) United States Plant Patent
Espin

(10) Patent No.: US PP34,723 P2
(45) Date of Patent: Nov. 8, 2022

(54) GRAPEVINE PLANT NAMED 'GENSEL 2'

(50) Latin Name: *Vitis vinifera*
Varietal Denomination: 'GENSEL 2'

(71) Applicant: Special New Fruit Licensing Mediterráneo S.L. (SNFL Mediterráneo S.L.), Murcia (ES)

(72) Inventor: Juan Carreño Espin, Murcia (ES)

(73) Assignee: SPECIAL NEW FRUIT LICENSING MEDITERRÁNEO S.L.(SNFL MEDITERRÁNEO S.L.), Murcia (ES)

( * ) Notice: Subject to any disclaimer, the term of this patent is extended or adjusted under 35 U.S.C. 154(b) by 0 days.

(21) Appl. No.: 17/576,280

(22) Filed: Jan. 14, 2022

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 5/0812; A01H 5/00; A01H 5/02; A01H 6/88
See application file for complete search history.

(56) References Cited

U.S. PATENT DOCUMENTS

PP21,316 P3 9/2010 Sheehan
PP23,125 P2 * 10/2012 Sheehan ..... A01H 6/88 Plt./205
PP33,449 P2 * 9/2021 Martinez ..... A01H 6/88 Plt./207

OTHER PUBLICATIONS

Listado de Solicitudes 2021 5 retrieved on Apr. 5, 2022 at https://www.aragon.es/documents/20127/29807078/26-11-2021+Listado+recopilatorio+de+variedades+frutales+solicitadas+para+incluir+en+los+Registros.pdf/de0d3c3b-4abf-9f72-e53e-62074aff0bfd?t=1637923374359, pp. 1 and 52. (Year: 2021).*

*Vitis* International Variety Catalogue for Sheegene 20, retrieved on Apr. 5, 2022 at file:///C:/Users/jhwu/Downloads/Passport%20data%20-%20VIVC%20prime%20name_SHEEGENE%2020%20(1).pdf, one page. (Year: 2022).*

U.S. Appl. No. 17/576,262, filed Jan. 14, 2022, Espin.

U.S. Appl. No. 17/576,287, filed Jan. 14, 2022, Espin.

Spanish Plant Varieties Office. List of Commercial Varieties. Dec. 21, 2021, one page.

Spanish Plant Varieties Office. List of Commercial Varieties. Dec. 21, 2021. (English Translation), one page.

* cited by examiner

*Primary Examiner* — June Hwu
(74) *Attorney, Agent, or Firm* — Dentons US LLP

(57) ABSTRACT

'GENSEL 2' is a new and distinct grapevine plant with novel characteristics that include good fertility and naturally loose bunches, nice and well-structured. The berries produced by 'GENSEL 2' are red and seedless with a very crisp texture and neutral flavor and no detectable seed traces. The berries produced by 'GENSEL 2' are very large, weighing 11-12 g/berry on average, and harvested in early September in Murcia Region (Spain).

1 Drawing Sheet

Latin name of the genus and species of the plant claimed: *Vitis vinifera.*

Cultivar denomination: 'GENSEL 2'.

BACKGROUND OF THE INVENTION

The present invention relates to a new distinct variety of seedless grapevine named 'GENSEL 2'. The new variety originated from a hybridization performed in Murcia, Spain during 2015 between '05-611-169' (U.S. Plant Pat. No. 33,449), as the pollen parent, and '9-704' (U.S. Plant Pat. No. 23,125), as the seed parent. Abortive seed traces were embryo cultured and the resulting plant was planted in an evaluation block during 2016. The first evaluation of the fruit produced by 'GENSEL 2' was performed during 2017. 'GENSEL 2' was first asexually propagated by field grafting dormant hardwood scions to 1103 Paulsen Rootstock (not patented) in 2018 in Murcia, Spain. Fruit from the resulting four grafted 'GENSEL 2' vines was first harvested in 2019.

All characteristics and distinctions remain true to form and are established and transmitted through succeeding propagations.

SUMMARY OF THE INVENTION

The following are the most outstanding and distinguishing characteristics of 'GENSEL 2'. 'GENSEL 2' produces very large, red (5 R3/4), seedless berries with a very crisp texture that are harvested in early September, in Murcia-Spain and weight on average 11-12 g/berry.

'GENSEL 2' is believed to be most similar to 'Sheegene 3' (U.S. Plant Pat. No. 21,316 P3) but differs in maturity. Specifically, 'GENSEL 2' matures in early September whereas 'Sheegene 3' matures in early August. The berries produced by 'GENSEL 2' have a globose shape while the berries produced by 'Sheegene 3' have an ovate shape. 'GENSEL 2' produces berries with a very firm texture with resistance to cracking whilst the 'Sheegene 3' berries are firm and less resistant to cracking. The new variety, 'GENSEL 2', has a lower fertility rate than 'Sheegene 3' (1.1 v. 1.3).

'GENSEL 2' can be distinguished from its male parent, '05-611-169', in that the new cultivar produces red-coloured (5R3/4) grapes while '05-611-169' produces white grapes. 'GENSEL 2' clusters are less heavy than '05-611-169' clusters (average 600 g v. 750 g). The bunches of 'GENSEL 2' are loose whilst the bunches of '05-611-169' have a medium compactness. The berries of 'GENSEL 2' have globose shape while the berries of '05-611-169' are obovoid.

'GENSEL 2' can be distinguished from its female parent, '9-704', in that the berries of 'GENSEL 2' have a globose shape whereas the berries of '9-704' have an oval shape. The bunches of 'GENSEL 2' are loose whilst the bunches of '9-704' have a medium compactness. The harvest time of 'GENSEL 2' is in early September whilst the harvest time of '9-704' is in early October. The new variety, 'GENSEL 2', has a lower fertility rate than '9-704' (1.1 v. 1.4).

BRIEF DESCRIPTION OF THE DRAWING

FIG. 1—Shows the form, foliage, and fruit of a 4-year-old 'GENSEL 2' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'GENSEL 2'. The detailed description was obtained between March and November using 4-year-old plants grown in the field in Murcia, Spain. The color references are to the Munsell Plant Tissue Color Book, 2012 Edition by Munsell Color.

Classification:

*Family*.—Vitaceae.
*Botanical*.—*Vitis vinifera*.
*Common name*.—Grapevine.
*Cultivar name*.—'GENSEL 2'.

Plant:

*Plant habit and growth*.—Semi-erect.
*Age at maturity*.—4 years old.
*Size* (*at maturity*).—Height: 225 cm. Width: 300 cm.
*Vigor*.—Medium.
*Productivity*.—Medium; 100 pound/vine; 40,000 pound/acre (this includes all the bunches).
*Rootstock*.—Name of rootstock: 1103 Paulsen Rootstock (not patented). Age of rootstock at time of grafting: one year old.

Trunk:

*Size*.—Diameter: 5.2 cm. Height (at measured diameter of 5.2 cm): 45 cm above the ground.
*Shape*.—Straight and cylindrical.
*Surface texture*.—Straight grained with the outer layer easily removed.
*Bark colour*.—Interior: 5YR3/4. Exterior: 7.5YR4/2.

Canes:

*Size*.—Diameter: 9.2 mm. Length: 140 cm.
*Surface texture*.—Mature cane: smooth, slightly ribbed. Immature cane: smooth, finely ribbed.
*Form* (*woody shoot cross section form*).—Pith in center with diaphragm at nodes.
*Color*.—Mature: 5 months, 5GY5/6 (anthocyanins 5R3/4). Immature: 4 weeks, 5GY6/6 (anthocyanins 5R3/4). Dorsal side of internodes: 2.5GY7/6. Ventral side of internodes: 5GY7/6. Dorsal side of nodes: 2.5GY7/6. Ventral side of nodes: 5GY7/6.
*Internode length* (*upper mature sun cane*).—10.75 cm.
*Internode width* (*upper mature sun cane*).—8.6 cm.
*Node width*.—12.5 mm.

Bud:

*Bud description*.—Winter bud: rounded, pointed; 7.5YR4/4. Green bud: rounded, pointed; 5GY6/6.
*Time of bud burst*.—12 March.
*Time of bud leaf burst*.—24 March.

Tendrils:

*Form*.—Mostly trifid.
*Size*.—Medium.
*Length*.—20 cm.
*Diameter*.—3 mm.
*Texture and distribution of tendril at each node beginning at base*.—Smooth, discontinuous, 0000000010010011001001001 1 (0 means no tendril at that node and 1 means there is tendril at the node).
*Color*.—Mature: 4 weeks, 2.5GY7/8. Immature: 10 days, 5GY5/6.
*Anthocynanin*.—Mature: absent. Immature: absent.

Growing tips (young shoot):

*Pubescence*.—Low density of prostrate hairs on the shoot tip.
*Color*.—5GY5/6.
*Anthocynanin*.—Absent.
*Shape*.—Fully open.
*Apex*.—Triangular.
*Form of tip*.—Fully open.
*Shoot attitude before tying*.—Semi-erect growth.

Leaves:

*Shape*.—Cuneiform.
*Density*.—Medium.
*Apex*.—Pointed.
*Base*.—Rounded.
*Number of lobes*.—5.
*Depth of upper lateral sinuses of mature leaves*.—Medium.
*Arrangement of lobes of upper lateral sinuses on mature leaves*.—Open.
*Margin*.—Irregular teeth.
*Length of teeth on margin*.—2 to 10 mm.
*Shape of teeth on margin*.—Both sides convex.
*Texture* (*mature leaf*).—Upper surface: smooth, slightly bullate along main veins. Lower surface: smooth.
*Size*.—Immature: Length: 7.3 cm, 10 days. Width: 7.8 cm, 10 days. Mature: Length: 16.3 cm, 4 weeks. Width: 16.4 cm, 4 weeks. Ratio of length/width of teeth (mature leaf): small.
*Color*.—Immature leaf: Upper surface: 5GY4/8 (anthocyanins 2.5YR3/4). Proportion of main veins of the upper leaf with anthocyanin coloration: low (up to the first bifurcation). Lower surface: 5GY5/6 (anthocyanins 2.5YR3/4). Mature leaf: Upper surface: 7.5GY3/4. Lower surface: 5GY5/4. Autumn coloration: Upper surface: 2.5Y7/8. Lower surface: 2.5Y7/8.
*Venation*.—Pattern: palmate (veins on upper leaf are flat; veins on lower leaf are raised). Length of middle vein in mature leaves: 10.75 cm. Color: Upper surface: 2.5GY7/6. Lower surface: 2.5GY7/6.
*Petiolar sinus*.—Mostly half overlapped, lyre shaped.
*Petiole*.—Length: 10 cm. Diameter: 3 cm. Color: 5GY7/8, anthocyanins 10R5/4.

Floral cluster:

*General description and location*.—Mostly 6$^{th}$ node, 10% without shoulders.

*Quantity of inflorescences per cluster*.—445.

*Size*.—Length: 19 cm. Width: 8 cm hanging; 14 cm shoulders spread.

*Peduncle*.—Length: 5.25 cm.

*Inflorescences*.—Hermaphroditic.

*Stamens*.—2.35 mm, straight.

*Anthers*.—Small, nondescript.

*Date of bloom: start*.—10 May, 50%: 14 May, 100%: 17 May.

*Pollen amount*.—Sparse.

*Calyptra*.—5 segments, complete separation.

*Calyptra color*.—2.5GY5/8.

Fruit:

*Time of year of commercial harvest and shipment*.—September.

*Time of beginning of berry ripening*.—Late.

*Keeping quality*.—After 30 days of refrigerated storage the variety does not show symptoms of dehydration. The berries keep their original color and are very crisp.

Cluster (primary bunches):

*Generally size*.—Medium (600 g).

*Length* (*without peduncle*).—20 cm.

*Width*.—13 cm hanging and 20 cm with shoulders spread.

*Density*.—Tight.

*Peduncle length*.—4.6 cm.

*Peduncle diameter*.—5.6 mm.

*Peduncle color*.—2.5GY6/6.

*Number of berries per cluster*.—67 (on average).

*Berry*.—Size: very large (11.2 g). Diameter: 25.7 mm. Length: 26.5 mm. Shape: globose. Uniformity: unifom. Brix content: 19.7° Brix. Tiritable acidity: 0.427. Skin color (without bloom): 5R3/4. Skin color (with bloom): 5R3/6. Pedicel: Length: 7.4 mm. Diameter: 2.6 mm. Color: 2.5GY7/6. Strength of attachment to berry: very strong (10%).

Cluster (secondary bunches):

*Generally size*.—Medium (173 g).

*Length* (*without peduncle*).—7.9 cm.

*Width*.—8.9 cm hanging and 11.5 cm with shoulders spread.

*Density*.—Medium.

*Peduncle*.—Length: 4.8 cm. Diameter: 3.4 cm. Color: 2.5GY7/6.

*Number of berries per cluster*.—50 (on average).

*Berry*.—Size: large (8 g). Diameter: 24 mm. Length: 22.7 mm. Shape: globose. Uniformity: uniform. Brix content: 21° Brix. Tiritable acidity: 0.4. Skin color (without bloom): 5R3/4. Skin color (with bloom): 5R3/6. Pedicel: Length: 6 mm. Diameter: 2.6 mm. Color: 2.5GY7/6. Strength of attachment to berry: very strong (9%).

Berry flesh:

*Color*.—2.5GY8/6.

*Juice, color*.—2.5GY7/4.

*Juice production*.—Very high, 44%.

*Thickness of skin*.—Medium.

*Flavor*.—Neutral.

*Fragrance*.—Neutral, a herbaceous hint.

*Texture*.—Crunchy, very firm.

*Seeds*.—Non detectable.

*Use*.—Table grape.

Disease and insect resistance: This cultivar is susceptible to the main diseases of its species, such as *Erysiphe necator, Plasmopara viticola, Botrytis cinerea, Daktulosphaira vitifoliae, Ceratitis capitata, Planococcus ficus, Planococcus citri, Empoasca vitis*.

What is claimed is:

1. A new and distinct variety of grapevine named 'GENSEL 2' as shown and described herein.

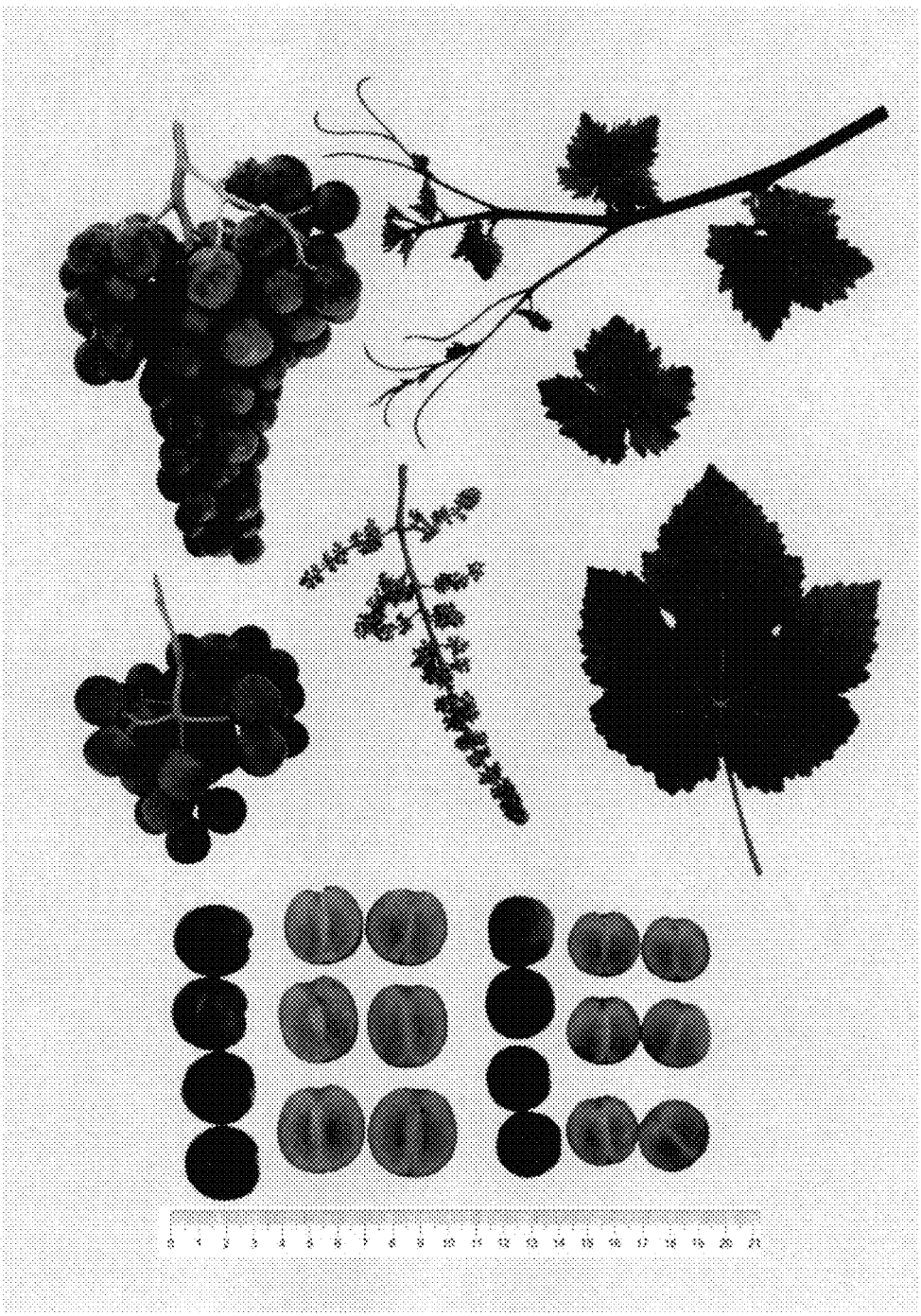

* * * * *